(12) United States Patent
Shang et al.

(10) Patent No.: US 11,379,980 B2
(45) Date of Patent: Jul. 5, 2022

(54) IMAGE PROCESSING METHOD, APPARATUS, ELECTRONIC DEVICE AND STORAGE MEDIUM

(71) Applicant: BEIJING BAIDU NETCOM SCIENCE TECHNOLOGY CO., LTD., Beijing (CN)

(72) Inventors: Fangxin Shang, Beijing (CN); Yehui Yang, Beijing (CN); Lei Wang, Beijing (CN); Yanwu Xu, Beijing (CN)

(73) Assignee: BEIJING BAIDU NETCOM SCIENCE TECHNOLOGY CO., LTD.

( * ) Notice: Subject to any disclaimer, the term of this patent is extended or adjusted under 35 U.S.C. 154(b) by 78 days.

(21) Appl. No.: 17/097,632

(22) Filed: Nov. 13, 2020

(65) Prior Publication Data
US 2021/0192728 A1 Jun. 24, 2021

(30) Foreign Application Priority Data
Jun. 24, 2020 (CN) .......................... 202010589818.7

(51) Int. Cl.
*G06K 9/00* (2022.01)
*G06T 7/00* (2017.01)
*A61B 3/12* (2006.01)

(52) U.S. Cl.
CPC .............. *G06T 7/0012* (2013.01); *A61B 3/12* (2013.01); *G06T 2207/20024* (2013.01);
(Continued)

(58) Field of Classification Search
CPC ......... G06T 7/0012; G06T 2207/20024; G06T 2207/20076; G06T 2207/20081;
(Continued)

(56) References Cited

U.S. PATENT DOCUMENTS

| 10,460,150 B2 | 10/2019 | Jackson et al. |
| 2002/0052551 A1* | 5/2002 | Sinclair .................. G16H 40/67 128/920 |

(Continued)

FOREIGN PATENT DOCUMENTS

| CN | 109686444 A | 4/2019 |
| CN | 109978071 A | 7/2019 |

(Continued)

OTHER PUBLICATIONS

Cs231n—Train Neural Network, Activation Functions, Data Pre-processing, Weight Initialization, Batch Normalization, Hyperparameter Optimization, Regularization, Transfer Learning, Aug. 5, 2018, pp. 1-10.

*Primary Examiner* — Van D Huynh
(74) *Attorney, Agent, or Firm* — Dilworth IP, LLC (57) ABSTRACT

The present application discloses an image processing method, an apparatus, an electronic device and a storage medium. A specific implementation is: acquiring an image to be processed; acquiring a grading array according to the image to be processed and a grading network model, where the grading network model is a model pre-trained according to mixed samples, the number of elements contained in the grading array is C−1, C is the number of lesion grades, C lesion grades include one lesion grade without lesion and C−1 lesion grades with lesion, and a kth element in the grading array is a probability of a lesion grade corresponding to the image to be processed being greater than or equal to a kth lesion grade, where $1 \leq k \leq C-1$, and k is an integer; determining the lesion grade corresponding to the image to be processed according to the grading array.

19 Claims, 4 Drawing Sheets

(52) U.S. Cl.
CPC ............... *G06T 2207/20076* (2013.01); *G06T 2207/20081* (2013.01); *G06T 2207/20084* (2013.01); *G06T 2207/30041* (2013.01)

(58) Field of Classification Search
CPC . G06T 2207/20084; G06T 2207/30041; G06T 7/11; A61B 3/12; G16H 30/40; G16H 50/20
USPC .......................................................... 382/128
See application file for complete search history.

(56) References Cited

U.S. PATENT DOCUMENTS

| | | | | |
|---|---|---|---|---|
| 2015/0110368 | A1* | 4/2015 | Solanki | G06V 10/50 382/128 |
| 2018/0315193 | A1* | 11/2018 | Paschalakis | G06K 9/6269 |
| 2019/0110753 | A1* | 4/2019 | Zhang | G06N 3/084 |
| 2019/0114771 | A1* | 4/2019 | Zhang | G06T 7/0014 |
| 2020/0085290 | A1* | 3/2020 | Wang | A61B 3/0025 |
| 2020/0234445 | A1* | 7/2020 | Lv | G06T 7/0012 |
| 2021/0224977 | A1* | 7/2021 | Jia | G16H 50/20 |
| 2021/0407656 | A1* | 12/2021 | Cheng | G16H 50/20 |

FOREIGN PATENT DOCUMENTS

| | | |
|---|---|---|
| CN | 110033456 A | 7/2019 |
| CN | 110633758 A | 12/2019 |
| CN | 110956628 A | 4/2020 |
| CN | 111275121 A | 6/2020 |

* cited by examiner

IMAGE PROCESSING METHOD, APPARATUS, ELECTRONIC DEVICE AND STORAGE MEDIUM

CROSS-REFERENCE TO RELATED APPLICATION

This application claims priority to Chinese Patent Application No. 202010589818.7, filed on Jun. 24, 2020, which is hereby incorporated by reference in its entirety.

TECHNICAL FIELD

Embodiments of the present application relate to the fields of deep learning and image processing of artificial intelligence technology in the computer field and can be specifically used for fundus oculi image analysis, and particularly relate to an image processing method, an apparatus, an electronic device and a storage medium.

BACKGROUND

With the continuous development and progress of medical imaging technology and computer technology, medical image analysis has become an indispensable tool and technical means in medical research, clinical disease diagnosis and treatment.

In recent years, Deep Learning (DL) has rapidly developed into a research hotspot of automated medical image analysis. Since deep learning and convolutional neural networks rely on a large amount of directly related annotation data, the application of which requires high costs of data collection and annotation. At the same time, in a specific scenario, it is not feasible to collect a large amount of data of a specific type. Taking a grading task of disease severity as an example, an existing method requires a large amount of medical image data to be contained in each lesion grade; on the other hand, patients with higher lesion grades are rare in the population, and it is extremely difficult to acquire a large amount of training samples for high lesion grades.

SUMMARY

The present application provides an image processing method, an apparatus, an electronic device and a storage medium.

According to a first aspect of the present application, an image processing method is provided; the method includes:

acquiring an image to be processed;

acquiring a grading array according to the image to be processed and a grading network model, where the grading network model is a model pre-trained according to mixed samples, the number of elements contained in the grading array is C−1, C is the number of lesion grades, C lesion grades include one lesion grade without lesion and C−1 lesion grades with lesion, and a kth element in the grading array is a probability of a lesion grade corresponding to the image to be processed being greater than or equal to a kth lesion grade, where $1 \leq k \leq C-1$, and k is an integer;

outputting the grading array.

According to a second aspect of the present application, an image processing apparatus is provided; the apparatus includes:

an acquiring module, configured to acquire an image to be processed;

a processing module, configured to acquire a grading array according to the image to be processed and a grading network model, where the grading network model is a model pre-trained according to mixed samples, the number of elements contained in the grading array is C−1, C is the number of lesion grades, C lesion grades include one lesion grade without lesion and C−1 lesion grades with lesion, and a kth element in the grading array is a probability of a lesion grade corresponding to the image to be processed being greater than or equal to a kth lesion grade, where $1 \leq k \leq C-1$, and k is an integer;

an output module, configured to output the grading array.

According to a third aspect of the present application, an electronic device is provided, including:

at least one processor; and a memory communicatively connected to at least one processor; where, the memory stores instructions capable of being executed by the at least one processor, and the instructions are executed by the at least one processor to enable the at least one processor to perform the method as described in any item of the first aspect.

According to a fourth aspect of the present application, a non-transitory computer readable storage medium storing computer instructions is provided, where the computer instructions are used to cause a computer to perform the method as described in any item of the first aspect.

According to the technology of the present application, an accurate judgment of the grading network model on the lesion grade corresponding to the medical image can be realized with a limited amount of training samples.

It should be understood that what is described in this section is not intended to identify key or important features of embodiments of the present application, nor is it used to limit the scope of the present application. Other features of the present application will become easy to understand by the following description.

BRIEF DESCRIPTION OF DRAWINGS

The drawings are used for better understanding of the solutions and do not constitute a limitation of the present application. Among them.

DESCRIPTION OF EMBODIMENTS

Exemplary embodiments of the present application are described below in conjunction with the drawings, where various details of the embodiments of the present application are included to facilitate understanding, and should be considered as merely exemplary. Therefore, it should be recognized by those of ordinary skills in the art that various changes and modifications can be made to the embodiments described herein without departing from the scope and spirit of the present application. Also, for the sake of clarity and conciseness, descriptions of well-known functions and structures are omitted in the following description.

Due to the shortage of professional imaging doctors and the imperfect basic medical and health conditions, there are still a large number of patients who cannot benefit from medical image screening technology and miss the optimal time of disease diagnosis and treatment. Therefore, how to use computer technology to automatically screen diabetic retinopathy has attracted the attention of medical treatment, computer science, artificial intelligence and other fields, and has great research significance and practical value.

Considering that deep learning relies on a large amount of directly related annotation data, the application thereof requires high costs of data collection and annotation. At the same time, in a specific scenario, it is not feasible to collect a large amount of data of a specific type. Taking a grading task of disease severity as an example, an existing method requires a large amount of medical image data to be contained in each lesion grade; on the other hand, patients with higher lesion grades are rare in the population, and it is extremely difficult to acquire a large amount of training samples for high lesion grades.

Based on the above problems, the present application provides an image processing method, an apparatus, an electronic device and a storage medium, which can realize an accurate judgment of a model on a lesion grade corresponding to a medical image with a limited amount of training samples based on computer vision technology and data amplification technology.

The image processing solutions provided by the present application are applied to the fields of deep learning and image processing of artificial intelligence technology and can be specifically used for fundus oculi image analysis, and are suitable for but not limited to an electronic device with a computing function, such as a computer, a server.

Detailed embodiments are adopted in the following to illustrate how a grading network model is applied in the embodiments of the present application.

Figure 1:
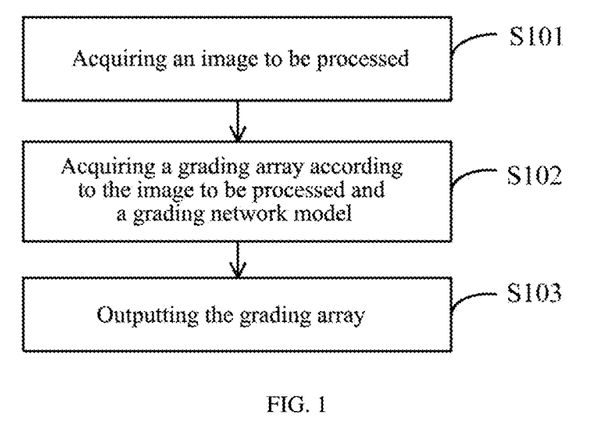
FIG. 1 is a schematic diagram according to a first embodiment of the present application.

FIG. 1 is a schematic diagram according to a first embodiment of the present application. This embodiment provides an image processing method, which can be performed by an image processing apparatus, where the image processing apparatus may be an electronic device with a computing function, such as a computer or a server, or the image processing apparatus may be a chip in an electronic device with a computing function.

As shown in FIG. 1, the image processing method includes the following steps:

S101: acquiring an image to be processed.

In the present application, the image to be processed can be an image collected for analyzing whether there is a certain lesion in a human body or an animal body. For example, the image to be processed may be a fundus oculi image used for judging diabetic retinopathy, or a chest image used for judging whether there is pulmonary tuberculosis, and so on, which is not limited in the present application.

The image to be processed can be collected by medical imaging equipment. For example, it may be a fundus oculi image collected by a Baidu AI fundus screening machine. The medical imaging equipment collects images and converts them into image data. It should be understood that the image to be processed can be either an image showing that there is no lesion in a human body or an animal body, or an image showing that there is lesion in a human body or an animal body. The image showing that there is lesion in a human body or an animal body may include a diagnostic marker area (or a lesion area) for diagnosing a lesion grade and other areas without diagnostic markers. Whether there is lesion can be determined by judging whether there is a diagnostic marker area, and the lesion grade, that is severity of the lesion, can also be determined by analyzing the diagnostic marker area.

S102: acquiring a grading array according to the image to be processed and a grading network model.

The grading network model is a model pre-trained according to mixed samples, the number of elements contained in the grading array is C−1, C is the number of lesion grades, C lesion grades include one lesion grade without lesion and C−1 lesion grades with lesion, and a kth element in the grading array is a probability of the lesion grade corresponding to the processed image being greater than or equal to a kth lesion grade, where 1≤k≤C−1, and k is an integer. For example, the following formula is adopted:

$$P_k = Pr(y \geq k|x), k=1, \ldots, C-1.$$

That is, a value of the kth element of the grading array P (counted from 1) is the probability of the lesion grade corresponding to the image x to be processed being greater than or equal to k.

In practical applications, the grading network model can adopt any classical classification network, such as an Inception Construction, a Residual Network (ResNet), a Densely Connected Convolutional Network (DenseNet) and so on, or it can be a self-constructed classification network.

As for the mixed samples, it can be understood that the amount of samples corresponding to each lesion grade, especially the samples of high lesion grades, is small, so the small amount of current samples are amplified by sample mixing. Sample mixing, as one of the latest research achievements in the field of computer vision, can effectively improve the limitation of a limited amount of training samples on model performance. Based on the idea of sample mixing, the present application can create amplified samples, that is, mixed samples, as many as possible with a limited amount of training samples. Since the grading network model is a model pre-trained according to mixed samples, the most effective capture of a relationship between the medical image and the corresponding disease severity is realized with a limited amount of training samples, and the data cost of applying the model is reduced.

The elements in the grading array described above are a group of data arranged in order, where each element corresponds to a lesion grade. For example, the number C of lesion grades is equal to 5, and the five lesion grades include one lesion grade without lesion (Grade 0) and four lesion grades with lesion; and the four lesion grades with lesion are divided into Grade 1, Grade 2, Grade 3 and Grade 4 according to the lesion severity. At this time, the grading array includes C−1 elements, that is, 4 elements, and the value of k is 1, 2, 3 or 4.

As an example, the grading array may be [a, b, c, d], where a corresponds to a probability of the lesion grade corresponding to the image being greater than or equal to Grade 1, b corresponds to a probability of the lesion grade corresponding to the image being greater than or equal to Grade 2, c corresponds to a probability of the lesion grade corresponding to the image being greater than or equal to Grade 3, and d corresponds to a probability of the lesion grade corresponding to the image being greater than or equal to Grade 4. If it is known that the lesion grade corresponding to the image is Grade 3, since the lesion grade which is Grade 3 must be greater than or equal to Grade 1, Grade 2 and Grade 3, but not greater than or equal to Grade 4, all of probability values represented by a, b and c are 100%, while a probability value represented by d is 0%, and thus the grading array can be expressed as [1,1,1,0]. In the same way, the grading array can be expressed as [1,0,0,0] when the lesion grade corresponding to the image is known to be Grade 1; the grading array can be expressed as [1,1,0,0] when the lesion grade corresponding to the image is known to be Grade 2; the grading array can be expressed as [1,1,1,1] when the lesion grade corresponding to the image is known to be Grade 4; and when the lesion grade corresponding to the image is Grade 0, that is, there is no lesion, at this time, the lesion grade corresponding to the image must not be greater than or equal to Grade 1, Grade 2, Grade 3 and Grade 4, therefore, all of the probability values represented by a, b, c and d are 0%, and at this time, the grading array can be expressed as [0,0,0,0].

The grading network model transforms the image to be processed into a grading array, which not only reflects an intensity relationship between lesion grades, but also retains category difference information between different lesion grades, and has high output accuracy. In essence, a multi-classification task is decomposed into multiple bi-classification tasks.

In the prior art, a grading network model usually outputs a certain type or a certain grade. When there is a fault in the grading network model or the output result is inaccurate due to other reasons, an error between the output result and the actual result may be very large. For example, the lesion grade corresponding to an image is Grade 4, but the output result is Grade 0 due to the error of the grading network model or other reasons. At this time, if medical staff rely too much on the grading predicted result, the error between the predicted result and the actual result will be very large, and then the best treatment opportunity will be delayed, etc. Compared with the prior art, in the present application, when the grading network model is used for calculation, the grading network model can do calculation C−1 times respectively, that is, each probability value is calculated independently, so that even if there is a deviation between a calculated result and the actual result due to the error of the grading network model or other reasons at a time, the error between the calculated result and the actual result will not be too large. For example, the lesion grade corresponding to a certain image is Grade 4, however when the grading network model is doing calculation, there is a fault in one calculation, and output results are [1,1,1,0], [1,0,1,1] or [1,1,0.6,1], etc. When the medical staff view the output results, they can basically judge that the lesion grade corresponding to the image may be above Grade 3 or even Grade 4, or, they can find there is a problem in the calculated result, then recalculation, manual image reading or other remedial measures are performed to ensure the reliability of the calculated result.

S103: outputting the grading array.

Here, "outputting" can include but is limited to: displaying/presenting the grading array through a display device, such as a screen; or, sending the grading array to a terminal device for relevant personnel to view. The terminal device includes, for example, a user mobile phone, a computer, etc.

The grading array is outputted and presented to the medical staff who specially deal with medical images, and the medical staff determine the lesion grade corresponding to the image to be processed according to the grading array.

According to the image processing method of the embodiments of the present application, firstly, an image to be processed is acquired; then, a grouping vector is acquired according to the image to be processed and a grading network model, where the grading network model is a model pre-trained according to mixed samples, the number of elements contained in the grouping vector is C−1, C is the number of lesion grades, C lesion grades include one lesion grade without lesion and C−1 lesion grades with lesion, and a kth element in the grouping vector is a probability of a lesion grade corresponding to the image to be processed being greater than or equal to a kth lesion grade, where $1 \leq k \leq C-1$, and k is an integer; finally, the grouping vector is outputted. Since the grading network model is a model pre-trained according to mixed samples, an accurate judgment of the grading network model on the lesion grade corresponding to the medical image is realized with a limited amount of training samples, and the data cost of applying the model is reduced. In addition, in the present application, the correlation relationship between the image to be processed and the lesion grades is considered, and the probabilities presenting that the lesion grade corresponding to the image to be processed being greater than or equal to the lesion grades, respectively, are outputted, thereby ensuring the reliability of the calculated result and further improving the accuracy of predicting the lesion grade.

In the above embodiments, since the grading network model needs to output an array formed by multiple probability values, and each probability value ranges from 0 to 1, the grading network model described above can be a grading network model with a sigmoid activation function. That is, an activation function layer is added at an output end of the grading network model, and an output of the grading network model is taken as an input of the activation function layer; and the data processed by the grading network model is mapped to between 0 and 1 by the activation function layer. That is to say, the output result of the grading network model is normalized by the sigmoid activation function.

Figure 2:
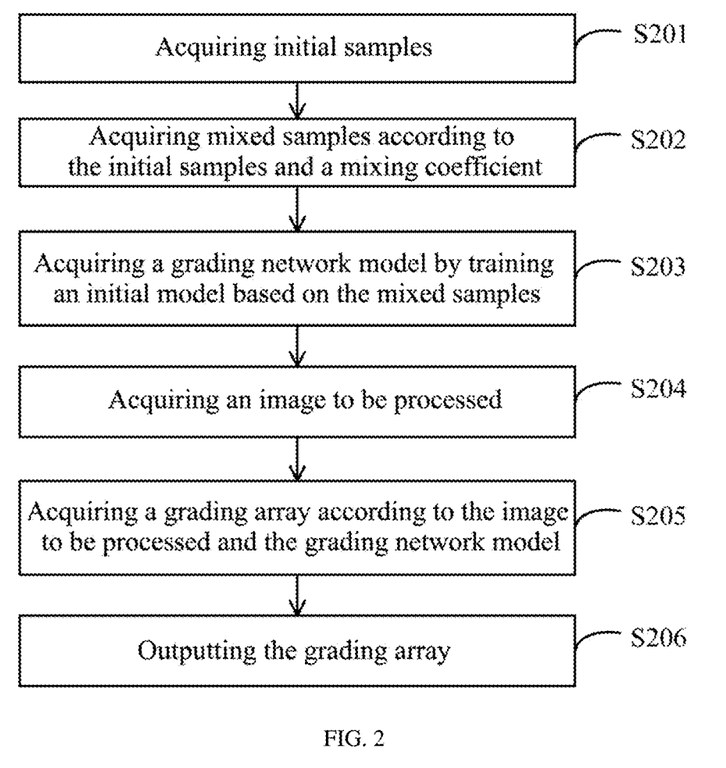
FIG. 2 is a schematic diagram according to a second embodiment of the present application.

Next, a training process of the grading network model described above will be introduced in conjunction with FIG. 2. Referring to FIG. 2, based on the process shown in FIG. 1, the image processing method can include:

S201: acquiring initial samples.

The initial samples are annotated with lesion grades. For example, the initial samples may be representative or universal images which are actually collected and which correspond to the lesion grades, and the corresponding lesion grades have been determined through medical practice.

S202: acquiring mixed samples according to the initial samples and a mixing coefficient.

Figure 3:
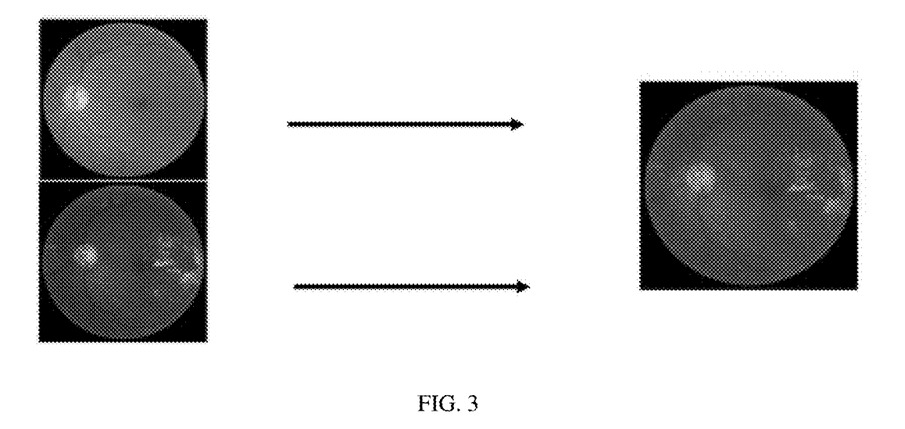
FIG. 3 is a schematic diagram of sample mixing in an image processing method according to an embodiment of the present application.

In combination with the mixing coefficient, the mixed samples are acquired by performing sample mixing processing on the initial samples, as shown in FIG. 3. For example, in a specific implementation, a mixed sample is acquired by performing sample mixing processing on two initial samples according to the following formula:

$$Mix = \lambda * Img_1 + (1-\lambda) * Img_2,$$

where the two initial samples are respectively expressed as $Img_1$ and $Img_2$, the mixed sample is expressed as Mix, and $\lambda \in [0,1]$ is the mixing coefficient.

It should be understood that a sum of mixing coefficients used to acquire one mixed sample is a fixed value, for example, the fixed value is 1.

S203: acquiring a grading network model by training an initial model based on the mixed samples.

In applications, the grading network model can be acquired by constructing and training the initial model with deep learning technology. The training data used to train the initial model includes the mixed samples described above. In this way, the reliability of the trained grading network model can be improved.

In addition, a target array, that is, an expected output, can be established through the known lesion grades. The number of elements contained in the target array is C−1, and the kth element in the target array is a probability of a lesion grade corresponding to an initial sample being greater than or equal to the kth lesion grade. It can be understood that conceptually speaking, the target array here is the same as the grading array mentioned above, and the reason for distinguishing different names is to distinguish different stages, where the grading array is an array acquired in an application stage of the grading network model, and the target array is an array used in a training stage of the grading network model.

It can be seen from the above discussion that the target array can be [0,0,0,0] when the lesion grade is Grade 0, and [1,0,0,0] when the lesion grade is Grade 1, and so on, that is, a correspondence between mixed samples and target arrays can be established through lesion grades.

For example, when the number C of lesion grades is equal to 5, the correspondence between the mixed samples and the target arrays can be established according to a rule as shown in Table 1.

TABLE 1

| Lesion grade | Target array |
| --- | --- |
| 0 | [0, 0, 0, 0] |
| 1 | [1, 0, 0, 0] |
| 2 | [1, 1, 0, 0] |
| 3 | [1, 1, 1, 0] |
| 4 | [1, 1, 1, 1] |

In a specific training process, a gradient descent method can be used to adjust model parameters according to a difference between a model output array and the target array, so as to reduce the difference between the model output array and the target array. When the difference between the model output array and the target array is reduced to be within an allowable error range, it can be determined that the training of the grading network model has been completed.

S204: acquiring an image to be processed.

S205: acquiring a grading array according to the image to be processed and the grading network model.

S206: Outputting the grading array.

S204 to S206 are similar to S101 to S103, and will not be described here again.

It should be further noted that in the embodiments of the present application, it is only necessary to ensure that S201 to S203 occur before S205, and the execution sequence with S204 is not limited in the embodiments of the present application.

In some embodiments, the acquiring the mixed samples according to the initial samples and the mixing coefficient of S202 can include: encoding and processing the initial samples to acquire target arrays; acquiring the mixed samples according to the target arrays and the mixing coefficient.

As an example, still taking C equal to 5 as an example, the correspondence between the mixed samples and the initial samples is shown in Table 2:

TABLE 2

| Mixed sample | | Initial sample B | | | | |
| --- | --- | --- | --- | --- | --- | --- |
| | | Grade 0 | Grade 1 | Grade 2 | Grade 3 | Grade 4 |
| Initial sample A | Grade 0 | [0, 0, 0, 0] | [1 − λ, 0, 0, 0] | [1 − λ, 1 − λ, 0, 0] | [1 − λ, 1 − λ, 1 − λ, 0] | [1 − λ, 1 − λ, 1 − λ, 1 − λ] |
| | Grade 1 | [λ, 0, 0, 0] | [1, 0, 0, 0] | [1, 1 − λ, 0, 0] | [1, 1 − λ, 1 − λ, 0] | [1, 1 − λ, 1 − λ, 1 − λ] |
| | Grade 2 | [λ, λ, 0, 0] | [1, λ, 0, 0] | [1, 1, 0, 0] | [1, 1, 1 − λ, 0] | [1, 1, 1 − λ, 1 − λ] |
| | Grade 3 | [λ, λ, λ, 0] | [1, λ, λ, 0] | [1, 1, λ, 0] | [1, 1, 1, 0] | [1, 1, 1, 1 − λ] |
| | Grade 4 | [λ, λ, λ, λ] | [1, λ, λ, λ] | [1, 1, λ, λ] | [1, 1, 1, λ] | [1, 1, 1, 1] |

More broadly, the correspondence between the mixed samples and the initial samples can be expressed by the following formula:

$$y_{enc}^{k} = \lambda * y_{enc1}^{k} + (1-\lambda) * y_{enc2}^{k},$$

where $y_{enc}^{k}$ represents a kth element of a target array corresponding to a mixed sample $y_{enc}$, and its value is determined by a kth element $y_{enc1}^{k}$ of a target array corresponding to an initial sample A and a kth element $y_{enc2}^{k}$ of a target array corresponding to an initial sample B as well as a mixing coefficient λ. For example, when both of $y_{enc1}^{k}$ and $y_{enc2}^{k}$ are 1, $y_{enc}^{k}$ is 1 regardless of the mixing coefficient λ.

Considering that the mixed samples acquired by mixing the initial sample A and the initial sample B and by mixing the initial sample B and initial sample A are the same, Table 2 can be simplified, as shown in Table 3:

TABLE 3

| Mixed sample | | Initial sample B | | | | |
| --- | --- | --- | --- | --- | --- | --- |
| | | Grade 0 | Grade 1 | Grade 2 | Grade 3 | Grade 4 |
| Initial sample A | Grade 0 | [0, 0, 0, 0] | — | — | — | — |
| | Grade 1 | [λ, 0, 0, 0] | [1, 0, 0, 0] | — | — | — |
| | Grade 2 | [λ, λ, 0, 0] | [1, λ, 0, 0] | [1, 1, 0, 0] | — | — |

TABLE 3-continued

| Mixed sample | Initial sample B | | | | |
|---|---|---|---|---|---|
| | Grade 0 | Grade 1 | Grade 2 | Grade 3 | Grade 4 |
| Grade 3 | [λ, λ, λ, 0] | [1, λ, λ, 0] | [1, 1, λ, 0] | [1, 1, 1, 0] | — |
| Grade 4 | [λ, λ, λ, λ] | [1, λ, λ, λ] | [1, 1, λ, λ] | [1, 1, 1, λ] | [1, 1, 1, 1] |

In addition, the images mentioned above, including the image to be processed and/or the initial samples, can be an image acquired after being preprocessed, where a preprocessing method can include but is not limited to at least one of the following: data normalization, Gaussian filtering and median filtering, etc. The purpose of normalization is to normalize images with different shades to the same range, for example, z-score normalization. And the function of Gaussian filtering and median filtering is to highlight physiological structures and lesion areas in the images. Therefore, before acquiring the grading array according to the image to be processed and the grading network model, the method further includes: preprocessing the image to be processed. Accordingly, the acquiring the grading array according to the image to be processed and the grading network model can include: acquiring the grading array according to the preprocessed image and the grading network model. In this embodiment, the image to be processed is preprocessed and thus has clearer physiological structure and lesion area, and then the accuracy of the grading network model can be improved.

On the basis of the embodiments described above, further, after acquiring the grading array through the grading network model, further data processing can be performed for the grading array. For example, the lesion grade corresponding to the grading array is outputted on the basis of considering probability values in the grading array. The following is an explanation in conjunction with FIG. 4.

Figure 4:
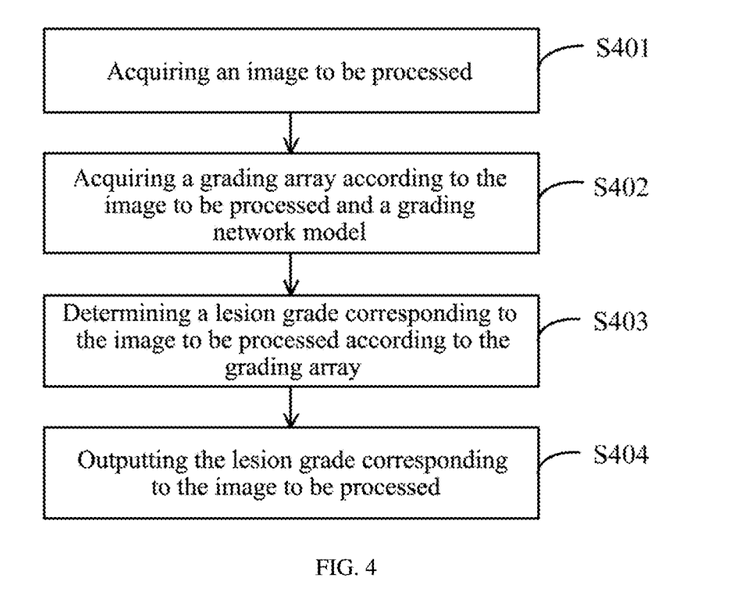
FIG. 4 is a schematic diagram according to a third embodiment of the present application.

Referring to FIG. 4, an image processing method provided by an embodiment of the present application includes the following steps:

S401: acquiring an image to be processed.

S402: acquiring a grading array according to the image to be processed and a grading network model.

S403: determining a lesion grade corresponding to the image to be processed according to the grading array.

S404: outputting the lesion grade corresponding to the image to be processed.

S401 and S402 correspond to the above S101 and S102 respectively. The specific implementation thereof is the same as that of the embodiments described above, and the same beneficial effects can be achieved. To avoid repetition, description thereof will not be repeated here.

In this embodiment of the present application, after acquiring the grading array, the lesion grade corresponding to the image to be processed is further determined and outputted according to the grading array, thereby further simplifying an image reading process and further improving the image reading efficiency.

In some embodiments, the determining the lesion grade corresponding to the image to be processed according to the grading array of S403 can include: acquiring a probability sum of the elements in the grading array; determining the lesion grade corresponding to the image to be processed according to a preset mapping relationship and the probability sum. The preset mapping relationship contains a correspondence between the lesion grade and the probability sum.

Since the elements in the grading array are each a probability value, the probability values corresponding to the elements are added to acquire the probability sum. Then, taking the probability sum as a query condition, the lesion grade corresponding to the image to be processed is queried in the preset mapping relationship.

In this embodiment of the present application, the lesion grade corresponding to the image to be processed is queried in the preset mapping relationship based on the probability sum by calculating the probability sum of the elements of the grading array, so that the correlation relationship between the lesion grades can be fully considered to ensure the reliability of a processing result.

Optionally, in order to fully consider the correlation relationship between the lesion grades to ensure the reliability of the processing result, before determining the lesion grade corresponding to the image to be processed according to the grading array of S403, the method further includes: selecting C−1 segmentation points between an interval [0, C−1] and segmenting the interval [0, C−1] to form C subintervals; establishing a correspondence between C lesion grades and the C subintervals. Accordingly, the determining the lesion grade corresponding to the image to be processed according to the preset mapping relationship and the probability sum can include: querying in the C subintervals with the probability sum as the query condition, and determining a target subinterval containing the probability sum; determining a lesion grade corresponding to the target subinterval as the lesion grade corresponding to the image to be processed.

The selecting the C−1 segmentation points between the interval [0, C−1] and segmenting the interval [0, C−1] can further include: selecting [a+i] as segmentation points to segment the interval [0, C−1], where 0<a<1, i=0, . . . , C−2. An optimization algorithm which is suitable for a non-differentiable function, such as a downhill simplex method (Nelder-Mead), can be used with maximizing a position-sensitive classification accuracy index (Kappa) as an optimization objective, so as to ensure that the value of a is reduced under the condition of meeting classification requirements, thus increasing a span of an interval corresponding to a lesion grade with lesion, and further helping to map the lesion grade corresponding to the image to the corresponding subinterval more accurately, thereby further improving the accuracy of predicting the lesion grade.

Specifically, an example in which the number of lesion grades C is 5 and a=0.5 is taken for further explanation. Since [a+i] are selected as the segmentation points, it can be determined that dividing points in this embodiment of the present application are 0.5, 1.5, 2.5 and 3.5, respectively, so that an interval [0,4] can be divided into the following subintervals [0,0.5), [0.5,1.5), [1.5,2.5), [2.5,3.5) and [3.5, 4]. A lesion grade corresponding to the subinterval [0,0.5) is Grade 0, that is, when the probability sum is less than 0.5, it can be determined that the lesion grade corresponding to the image is a lesion grade without lesion. In the same way, a lesion grade corresponding to the subinterval [0.5,1.5) is Grade 1, a lesion grade corresponding to the subinterval

[1.5,2.5) is Grade 2, a lesion grade corresponding to the subinterval [2.5,3.5) is Grade 3, and a lesion grade corresponding to the subinterval [3.5,4] is Grade 4, thus the correspondence between the probability sums represented by the elements and the lesion grades is established.

Please refer to the following table. A specific process of determining the lesion grade corresponding to the image by the probability sum will be explained with a specific example below:

| Dividing point | Probability sum | Lesion grade |
|---|---|---|
| [0.5, 1.5, 2.5, 3.5] | 0.4 | 0 |
| | 1.4 | 1 |
| | 1.6 | 2 |
| | 2.6 | 3 |
| | 3.6 | 4 |

It can be seen from the above table that when the probability sum is 0.4, since this probability sum is contained in the subinterval [0,0.5), the corresponding lesion grade is Grade 0, where grading arrays with the probability sum of 0.4 may be [0.4,0,0,0], [0.1,0.2,0.1,0], [0,0.2,0.1,0.1], [0,0,0,0.4], etc. The embodiments of the present application determine the lesion grade corresponding to the image by considering the sum of the elements instead of according to a certain element alone. In this way, the reliability of the prediction result can be further improved.

For example, according to a conventional method, when the grading array is [0,0,0,0.4], since the probability of the lesion grade corresponding to the image being Grade 4 is the highest according to the calculation of the grading network model, the conventional method may correspond the corresponding lesion grade to Grade 4. However, according to the method provided by the embodiments of the present application, since the probabilities of the lesion grade corresponding to this image being greater than or equal to Grade 1, Grade 2, Grade 3 are all 0, it can be seen that the lesion grade which most likely correspond to this image should be Grade 0 instead of Grade 4. And the calculated result that the probability of being greater than or equal to Grade 4 is 0.4, is probably caused by a failure of the grading network model or other reasons. In the same way, it can be seen from the above table that when the probability sum is 1.4, it can be determined that the corresponding lesion grade is Grade 1, since this probability sum is contained in the subinterval [0.5,1.5); when the probability sum is 1.6, it can be determined that the corresponding lesion grade is Grade 2, since this probability sum is contained in the subinterval [1.5,2.5); when the probability sum is 2.6, it can be determined that the corresponding lesion grade is Grade 3, since this probability sum is contained in the subinterval [2.5,3.5); and when the probability sum is 3.6, it can be determined that the lesion grade is Grade 4, since this probability sum is contained in the subinterval [3.5,4].

In the embodiments of the present application, by calculating the probabilities of the lesion grade corresponding to the image being greater than or equal to various lesion grades, respectively, the lesion grade corresponding to the image can still be predicted by combining other probability values even if there are errors in some of the calculated probability values. Therefore the problem that the methods in the prior art have poor image processing effect is solved, and the reliability of image processing results is further improved.

Figure 5:
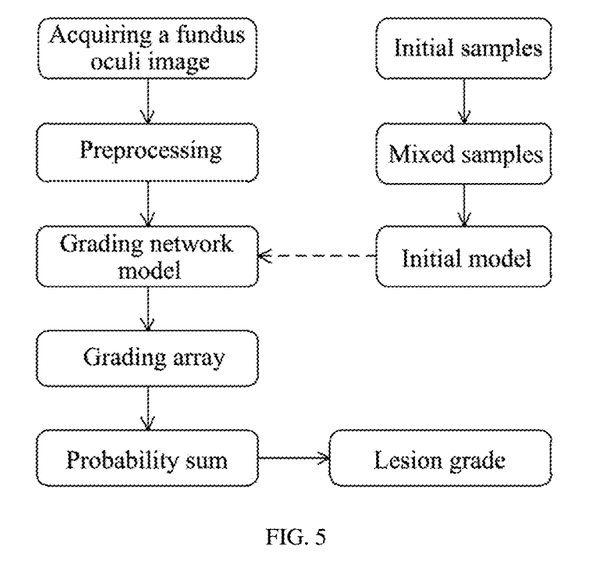
FIG. 5 is a schematic diagram of an application of an image processing method according to an embodiment of the present application.

Please refer to FIG. 5, FIG. 5 is a flow chart of the method described above applied to judging the lesion grade of diabetic retinopathy, which specifically includes the following steps: acquiring a fundus oculi image, and preprocessing the fundus oculi image; inputting the preprocessed image into a pre-trained grading network model; calculating by the grading network model and outputting a grading array; calculating a probability sum of elements in the grading array, and determining a lesion grade corresponding to the fundus oculi image according to the calculated probability sum and a preset mapping relationship. The grading network model is acquired according to mixed samples and an initial model, and the mixed samples are acquired by performing sample mixing processing on initial samples.

Figure 6:
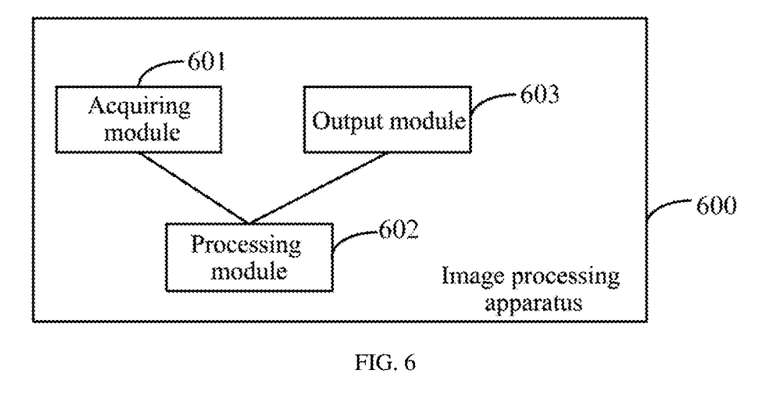
FIG. 6 is a schematic diagram according to a fourth embodiment of the present application.

FIG. 6 is a schematic diagram according to a fourth embodiment of the present application. This embodiment provides an image processing apparatus. As shown in FIG. 6, the image processing apparatus 600 includes: an acquiring module 601, a processing module 602 and an output module 603.

The acquiring module 601 is configured to acquire an image to be processed.

The processing module 602 is configured to acquire a grading array according to the image to be processed and a grading network model. The grading network model is a model pre-trained according to mixed samples, the number of elements contained in the grading array is C−1, C is the number of lesion grades, C lesion grades include one lesion grade without lesion and C−1 lesion grades with lesion, and a kth element in the grading array is a probability of a lesion grade corresponding to the image to be processed being greater than or equal to a kth lesion grade, where $1 \leq k \leq C-1$, and k is an integer.

The output module 603 is configured to output the grading array.

The image processing apparatus provided in this embodiment can be used to perform the method embodiments described above, and their implementations and technical effects are similar, which will not be repeated here.

Optionally, the acquiring module 601 can further be configured to acquire initial samples annotated with lesion grades. Correspondingly, the processing module 602 can further be configured to acquire the mixed samples according to the initial samples and a mixing coefficient; acquire the grading network model by training an initial model based on the mixed samples.

In some embodiments, when the processing module 602 is configured to acquire the mixed samples according to the initial samples and the mixing coefficient, the processing module 602 is specifically configured to: encode and process an initial sample to acquire a target array, the number of elements contained in the target array is C−1, and a kth element in the target array is a probability of a lesion grade corresponding to the initial sample being greater than or equal to a kth lesion grade; acquire a mixed sample according to the target array and the mixing coefficient.

Optionally, a sum of mixing coefficients used to acquire one mixed sample is a fixed value. For example, the fixed value is 1.

In the above embodiments, an output result of the grading network model is normalized by a sigmoid activation function.

Further, the processing module 602 can further be configured to: determine the lesion grade corresponding to the image to be processed according to the grading array after acquiring the grading array according to the image to be processed and the grading network model. Accordingly, the output module 603 can further be configured to: output the lesion grade corresponding to the image to be processed.

Further, when the processing module 602 is configured to determine the lesion grade corresponding to the image to be processed according to the grading array, the processing module 602 is specifically configured to: acquire a probability sum of the elements in the grading array; determine the lesion grade corresponding to the image to be processed according to a preset mapping relationship and the probability sum. The preset mapping relationship contains a correspondence between the lesion grade and the probability sum.

In some embodiments, the processing module 602 can further be configured to: preprocess the image to be processed; acquire the grading array according to the preprocessed image and the grading network model.

Optionally, a preprocessing method may include at least one of the following: data normalization, Gaussian filtering and median filtering, etc.

According to embodiments of the present application, the present application further provides an electronic device and a readable storage medium.

Figure 7:
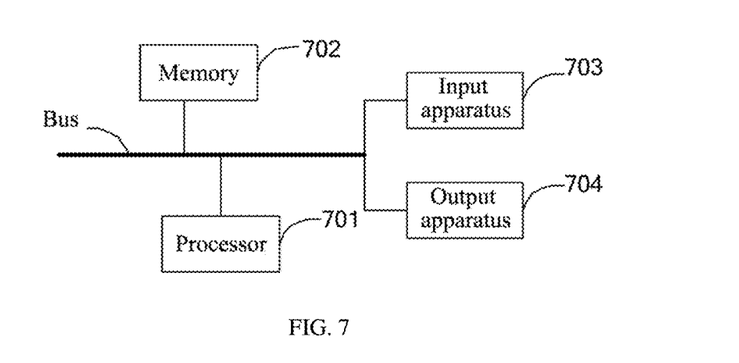
FIG. 7 is a block diagram of an electronic device for implementing an image processing method according to an embodiment of the present application.

As shown in FIG. 7, FIG. 7 is a block diagram of an electronic device for implementing an image processing method according to an embodiment of the present application. The electronic device is intended to represent various forms of digital computers, such as a laptop computer, a desktop computer, a workstation, a personal digital assistant, a server, a blade server, a mainframe computer, and other suitable computers. The electronic device can also represent various forms of mobile devices, such as a personal digital assistant, a cellular phone, a smart phone, a wearable device and other similar computing devices. The components shown herein as well as their connections and relationships and their functions are merely examples, and are not intended to limit the implementation of the present application described and/or claimed herein.

As shown in FIG. 7, the electronic device includes: one or more processors 701, a memory 702, and interfaces for connecting various components, including high-speed interfaces and low-speed interfaces. The various components are connected to each other by different buses, and can be installed on a common main board or mounted in other ways as required. The processor may process instructions executed within the electronic device, including instructions stored in or on the memory to display GUI graphical information on an external Input/Output apparatus, such as a display device coupled to an interface. In other implementations, multiple processors and/or multiple buses may be used with multiple memories, if needed. Similarly, multiple electronic devices can be connected, and each device provides some necessary operations (for example, as a server array, a group of blade servers, or a multiprocessor system). One processor 701 is taken as an example in FIG. 7.

The memory 702 is the non-transitory computer readable storage medium provided in the present application. The memory stores instructions executable by at least one processor to cause the at least one processor to execute the image processing method provided by the present application. The non-transitory computer readable storage medium of the present application stores computer instructions for causing a computer to execute the image processing method provided by the present application.

As a non-transitory computer readable storage medium, the memory 702 can be used for storing non-transitory software programs, non-transitory computer executable programs and modules, such as program instructions/modules corresponding to the image processing method in the embodiments of the present application (for example, the acquiring module 601, the processing module 602 and the output module 603 shown in FIG. 6). The processor 701 executes various functional applications and data processing of a server by running non-transitory software programs, instructions and modules stored in the memory 702, that is, realizes the image processing method in the method embodiments described above.

The memory 702 can include a program storing area and a data storing area, where the program storing area may store an operating system, an application program required by at least one function; the data storing area can store data created by the use of the electronic device for implementing the image processing method, etc. In addition, the memory 702 can include a high-speed random access memory, and may further include a non-transitory memory, such as at least one disk memory device, a flash memory device, or other non-transitory solid-state memory devices. In some embodiments, the memory 702 may optionally include memories remotely located with respect to the processor 701, and these remote memories may be connected to the electronic device for implementing the image processing method through a network. Examples of the network described above includes but are not limited to, the Internet, an intranet, a local area network, a mobile communication network and combinations thereof.

The electronic device for implementing the image processing method may further include: an input apparatus 703 and an output apparatus 704. The processor 701, the memory 702, the input apparatus 703, and the output apparatus 704 may be connected by a bus or other means. A connection by a bus is taken as an example in FIG. 7.

The input apparatus 703 can receive inputted digital or character information, and generate a key signal input related to user setting and function control of the electronic device used for implementing the image processing method, such as a touch screen, a keypad, a mouse, a track pad, a touch pad, an indicator stick, one or more mouse buttons, a trackball, a joystick and other input apparatuses. The output apparatus 704 may include a display device, an auxiliary lighting apparatus (e.g., an LED), a tactile feedback device (e.g., a vibration motor), etc. The display device may include, but is not limited to, a liquid crystal display (LCD), a light emitting diode (LED) display, and a plasma display. In some implementations, the display device may be a touch screen.

The various embodiments of the systems and techniques described herein may be implemented in digital electronic circuit systems, integrated circuit systems, dedicated ASIC (application specific integrated circuits), computer hardware, firmware, software, and/or combinations thereof. These various embodiments may include: being implemented in one or more computer programs that can be executed and/or interpreted on a programmable system including at least one programmable processor. The programmable processor may be a special or general programmable processor, and can receive data and instructions from a storage system, at least one input apparatus, and at least one output apparatus, and transmit data and instructions to the storage system, the at least one input apparatus, and the at least one output apparatus.

These computing programs (also called programs, software, software applications, or codes) include machine instructions of programmable processors, and can be implemented using high-level procedures and/or object-oriented programming languages, and/or assembly/machine languages. As used herein, the terms "machine-readable medium" and "computer-readable medium" refer to any computer program product, device, and/or apparatus (e.g., a magnetic disk, an optical disk, a memory, a programmable logic device (PLD)) for providing machine instructions and/or data to a programmable processor, including a machine-readable medium that receives machine instructions as machine-readable signals. The term "machine-readable signal" refers to any signal used for providing machine instructions and/or data to a programmable processor.

To provide interaction with users, the systems and techniques described herein can be implemented on a computer which has: a display device (e.g., a CRT (cathode ray tube) or LCD (liquid crystal display) monitor) for displaying information to users; as well as a keyboard and a pointing apparatus (e.g., a mouse or a trackball) through which users can provide inputs to the computer. Other kinds of apparatuses can also be used to provide interaction with users, for example, a feedback provided to a user can be any form of sensory feedback (e.g., visual feedback, auditory feedback, or tactile feedback); and can receive inputs from users in any form (including acoustic input, voice input or tactile input).

The systems and techniques described herein can be implemented in a computing system including background components (e.g., as a data server), or a computing system including middleware components (e.g., an application server), or a computing system including front-end components (e.g., a user computer with a graphical user interface or a web browser through which users can interact with implementations of the systems and techniques described herein), or a computing system including any combination of such background components, middleware components or front-end components. Components of the system can be connected to each other through digital data communication in any form or medium (e.g., a communication network). Examples of the communication network include: a local area networks (LAN), a wide area network (WAN) and the Internet.

A computer system may include a client and a server. The client and server are generally remote from each other and usually interact through a communication network. A relationship between the client and the server is generated by computer programs running on corresponding computers and having a client-server relationship with each other.

Figure 8:
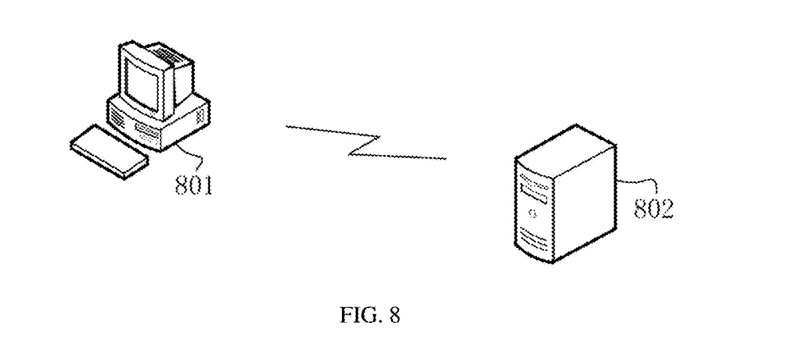
FIG. 8 is a diagram of a scenario in which an embodiment of the present application can be implemented.

FIG. 8 is a diagram of a scenario in which an embodiment of the present application can be implemented. As shown in FIG. 8, an image collection device 801 is configured to collect images, and a server 802 interacts with the image collection device 801 to implement the image processing method in any embodiment described above. After performing the image processing method described above, the server 802 outputs the grading array and/or the lesion grade corresponding to the image to be processed to the image collection device 801 for display.

Optionally, a terminal device may also be included. After performing the image processing method described above, the server 802 outputs the grading array and/or the lesion grade corresponding to the image to be processed to the terminal device, which are then displayed to relevant personnel through the terminal device. The image collection device 801 is illustrated by taking a computer as an example in FIG. 8, but the embodiments of the present application are not limited thereto.

According to the technical solutions of the embodiments of the present application, firstly, an image to be processed is acquired; then, a grading array is acquired according to the image to be processed and a grading network model, where the grading network model is a model pre-trained according to mixed samples, the number of elements contained in the grading array is C−1, C is the number of lesion grades, C lesion grades include one lesion grade without lesion and C−1 lesion grades with lesion, and a kth element in the grading array is a probability of a lesion grade corresponding to the image to be processed being greater than or equal to a kth lesion grade, where $1 \leq k \leq C-1$, and k is an integer; finally, the lesion grade corresponding to the image to be processed is determined according to the grading array. According to the present application, an accurate judgment of the grading network model on the lesion grade corresponding to a medical image is realized with a limited amount of training samples.

It should be understood that steps can be reordered, added or deleted for the various forms of processes shown above. For example, the steps described in the present application can be executed in parallel, sequentially or in a different order, so long as the desired result of the technical solution disclosed in the present application can be achieved, which is not limited herein.

The specific embodiments described above do not limit the protection scope of the present application. It should be understood by those skilled in the art that various modifications, combinations, sub-combinations and substitutions can be made according to design requirements and other factors. Any modification, equivalent substitution, improvements and others that are made within the spirit and principle of the present application shall be contained in the protection scope of the present application.

What is claimed is:

1. An image processing method, comprising:
   acquiring an image to be processed;
   acquiring a grading array according to the image to be processed and a grading network model, wherein the grading network model is a model pre-trained according to mixed samples, the number of elements contained in the grading array is C−1, C is the number of lesion grades, C lesion grades comprise one lesion grade without lesion and C−1 lesion grades with lesion, and a kth element in the grading array is a probability of a lesion grade corresponding to the image to be processed being greater than or equal to a kth lesion grade, wherein $1 \leq k \leq C-1$, and k is an integer;
   outputting the grading array.

2. The method according to claim 1, wherein before acquiring the grading array according to the image to be processed and the grading network model, the method further comprises:
   acquiring initial samples, wherein the initial samples are annotated with lesion grades;
   acquiring the mixed samples according to the initial samples and a mixing coefficient;
   acquiring the grading network model by training an initial model based on the mixed samples.

3. The method according to claim 2, wherein the acquiring the mixed samples according to the initial samples and the mixing coefficient comprises:
   encoding and processing an initial sample to acquire a target array, wherein the number of elements contained in the target array is C−1, and a kth element in the target array is a probability of a lesion grade corresponding to the initial sample being greater than or equal to a kth lesion grade, wherein $1 \leq k \leq C-1$, and k is an integer;
   acquiring a mixed sample according to the target array and the mixing coefficient.

4. The method according to claim 2, wherein a sum of mixing coefficients used to acquire one of the mixed samples is a fixed value.

5. The method according to claim 1, wherein an output result of the grading network model is normalized by a sigmoid activation function.

6. The method according to claim 1, wherein after acquiring the grading array according to the image to be processed and the grading network model, the method further comprises:
determining the lesion grade corresponding to the image to be processed according to the grading array;
outputting the lesion grade corresponding to the image to be processed.

7. The method according to claim 6, wherein the determining the lesion grade corresponding to the image to be processed according to the grading array comprises:
acquiring a probability sum of the elements in the grading array;
determining the lesion grade corresponding to the image to be processed according to a preset mapping relationship and the probability sum, wherein the preset mapping relationship comprises a correspondence between the lesion grade and the probability sum.

8. The method according to claim 1, wherein before acquiring the grading array according to the image to be processed and the grading network model, the method further comprises:
preprocessing the image to be processed;
accordingly, the acquiring the grading array according to the image to be processed and the grading network model comprises: acquiring the grading array according to the preprocessed image and the grading network model.

9. The method according to claim 8, wherein a preprocessing method comprises at least one of the following:
data normalization, Gaussian filtering and median filtering.

10. An image processing apparatus, comprising:
at least one processor; and
a memory communicatively connected to the at least one processor; wherein,
the memory stores instructions capable of being executed by the at least one processor, and the instructions are executed by the at least one processor, so that the at least one processor is configured to:
acquire an image to be processed;
acquire a grading array according to the image to be processed and a grading network model, wherein the grading network model is a model pre-trained according to mixed samples, the number of elements contained in the grading array is C−1, C is the number of lesion grades, C lesion grades comprise one lesion grade without lesion and C−1 lesion grades with lesion, and a kth element in the grading array is a probability of a lesion grade corresponding to the image to be processed being greater than or equal to a kth lesion grade, wherein 1≤k≤C−1, and k is an integer;
output the grading array.

11. The image processing apparatus according to claim 10, wherein the at least one processor is further configured to, before acquiring the grading array according to the image to be processed and the grading network model:
acquire initial samples, wherein the initial samples are annotated with lesion grades;
acquire the mixed samples according to the initial samples and a mixing coefficient;
acquire the grading network model by training an initial model based on the mixed samples.

12. The image processing apparatus according to claim 11, wherein the at least one processor is further configured to:
encode and process an initial sample to acquire a target array, wherein the number of elements contained in the target array is C−1, and a kth element in the target array is a probability of a lesion grade corresponding to the initial sample being greater than or equal to a kth lesion grade, wherein 1≤k≤C−1, and k is an integer;
acquire a mixed sample according to the target array and the mixing coefficient.

13. The image processing apparatus according to claim 11, wherein a sum of mixing coefficients used to acquire one of the mixed samples is a fixed value.

14. The image processing apparatus according to claim 10, wherein an output result of the grading network model is normalized by a sigmoid activation function.

15. The image processing apparatus according to claim 10, wherein the at least one processor is further configured to, after acquiring the grading array according to the image to be processed and the grading network model:
determine the lesion grade corresponding to the image to be processed according to the grading array;
output the lesion grade corresponding to the image to be processed.

16. The image processing apparatus according to claim 15, wherein the at least one processor is further configured to:
acquire a probability sum of the elements in the grading array;
determine the lesion grade corresponding to the image to be processed according to a preset mapping relationship and the probability sum, wherein the preset mapping relationship comprises a correspondence between the lesion grade and the probability sum.

17. The image processing apparatus according to claim 10, wherein the at least one processor is further configured to:
preprocess the image to be processed before acquiring the grading array according to the image to be processed and the grading network model;
acquire the grading array according to the preprocessed image and the grading network model.

18. The image processing apparatus according to claim 17, wherein a preprocessing method comprises at least one of the following:
data normalization, Gaussian filtering and median filtering.

19. A non-transitory computer readable storage medium storing computer instructions, wherein the computer instructions are used to cause a computer to perform the method according to claim 1.

* * * * *